United States Patent [19]

Kawada et al.

[11] Patent Number: 4,672,734
[45] Date of Patent: Jun. 16, 1987

[54] SUTURE NEEDLE AND ITS MANUFACTURING PROCESSES

[75] Inventors: Tsutomu Kawada, Chuo; Yasuo Nakamura, c/o Nakamura Co., Ltd., 3-3, Nihonbashi Honcho, Chuo-ku, both of Japan

[73] Assignee: Yasuo Nakamura, Tokyo, Japan

[21] Appl. No.: 830,926

[22] Filed: Feb. 19, 1986

[51] Int. Cl.[4] .................. B21D 39/00; B23D 17/00; A61B 17/06; B21G 1/00
[52] U.S. Cl. ...................................... 29/517; 29/418; 163/1; 128/339
[58] Field of Search .................. 128/339; 29/413, 414, 29/415, 418, 517; 163/1, 4, 5, 6

[56] References Cited

U.S. PATENT DOCUMENTS

| | | | |
|---|---|---|---|
| 383,733 | 5/1888 | Jenkins | 128/339 |
| 1,122,210 | 12/1914 | Lukens | 128/339 |
| 1,591,021 | 7/1926 | Davis | 128/339 |
| 1,695,887 | 12/1928 | Davis | 128/339 |
| 2,743,517 | 5/1956 | Everett | 29/418 |
| 3,173,200 | 3/1965 | Dunmire et al. | 29/414 |
| 3,611,551 | 10/1971 | Shave et al. | 128/339 |

Primary Examiner—Howard N. Goldberg
Assistant Examiner—Steven N. Nichols
Attorney, Agent, or Firm—Holman & Stern

[57] ABSTRACT

A large number of needle patterns are integrally associated with each other on an extended U-shaped metal plate. After that, a pointed end of individual needle patterns is formed, and a series of individual needle patterns are divided into a plurality of segmented needle bodies. Then, a suture is inserted into a hollow portion of the needle body. By closing both walls of the needle body, a suture needle can be produced one after another.

2 Claims, 38 Drawing Figures

Prior Art

Prior Art

SUTURE NEEDLE AND ITS MANUFACTURING PROCESSES

BACKGROUND OF THE INVENTION

1. Technical Field of the Invention

This invention relates to a suture needle and its manufacturing processes. More particularly, the suture needle is used for medical treatment, in which a suture is previously inserted and fixed within a needle body.

2. Description of the Prior Art

Conventionally, there are known two types of suture needles. According to a first type of suture needle, every time a needle is used, a suture is hooked in an aperture of a needle body. According to a second type, the suture is previously fixed in a hole formed at a front part of the needle body at the manufacturing stage. In the first type, every time the suture needle is used, sterilization is required and the suture may be disengaged from the aperture of the needle body, so that it is an old-fashioned type. Today, the second type is prevailing in advanced countries. That is, it is also a disposable type.

[I] FIGS. 8(a) to 8(d) show repective views of a first embodiment of a conventional suture needle which is frequently used today. Numeral 1 is semicircular needle body made of stainless steel, which comprises a fixing part 2 for fixing a suture 3 at an end of the needle body 1. As shown in 8(d), the fixing part 2 consists of a hole 2a formed in an axial direction of the needle body 1. The suture 3 is inserted into the hole 2a and firmly fixed therein by caulking means.

Figure 8B:
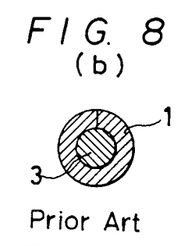
Figure 8C:
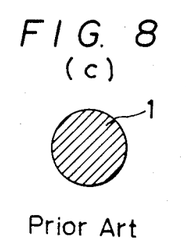
Figure 8D:
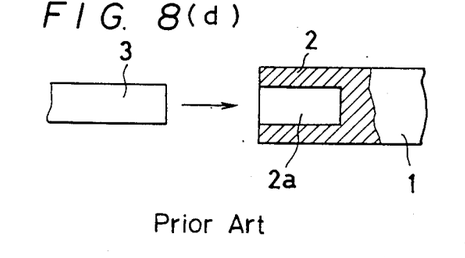

According to a conventional process for manufacturing needles, a stainless steel thin rod is cut off with a suitable length for a needle body. Then, the hole 2a is bored by laser processing, drilling or the like. Subsequently, the suture 3 is inserted into the hole 2a manually and fixed therein by caulking means.

The aforesaid prior art has the following disadvantages and inconveniences.

(1) The depth of the hole 2a for inserting the suture 3 therein is limited in view of boring operation, so that fixation of the suture in the hole 2a is not always complete. Accordingly, disengagement of the suture from the hole may occur easily. If caulking stress is too strong, the needle body 1 may be broken or deformed.

(2) Since the needle body is provided, at one end, with the hole for inserting the suture, the needle body is inclined to be broken in the proximity of the hole.

(3) Since the needle body except for the hole portion is of a solid construction, its resilience is relatively low. Accordingly, there grows the danger that a pointed end of the needle body may be broken and retain in a body during sewing operation. Such accident may cause a serious condition.

(4) After the hole has been bored and the suture has been fixed therein, it is no more possible to clean the interior of the hole. Accordingly, it is impossible to wipe away any foreign matter that may remain in the hole during boring operation.

(5) After the suture has been inserted in the hole, sterilization must be carried out, but an inserted part of the suture is inconvenient for a complete sterilization.

(6) The boring operation including laser processing, drilling or the like requires high accuracy, so that it is a cumbersome work. It is very difficult to obtain a bore of a very accurate diameter effective to insert the suture thereinto.

(7) It is also a very cumbersome work even for skilled workers to insert and fix a soft and thin suture into such a minute hole. The daily output of such conventional suture needles is so limited that the production cost is expensive and quality is not always uniform.

[II] A second embodiment of the prior art will be described with reference to FIG. 9(a) to FIG. 10(b), in which every time a suture is used, it must be engaged with an end of the suture needle.

Symbol B1 is a typical conventional suture needle body formed by a stainless steel rod, in which B2 is a hole means for inserting a suture therein and B3 is a pointed end of the suture needle body B1.

Figure 9:
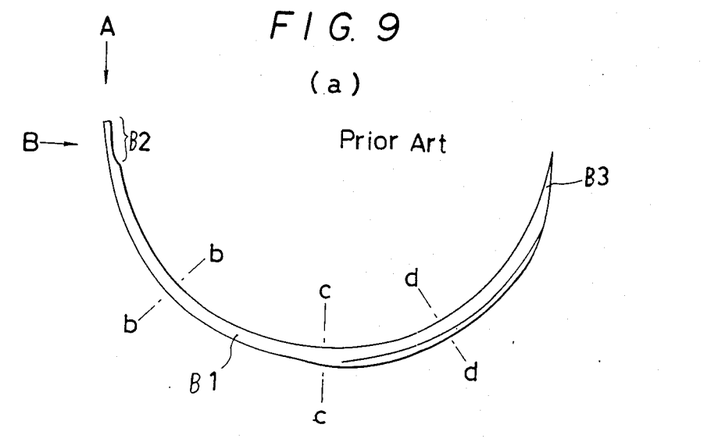
FIGS. 9(a) to 9(d) and FIGS. 10(a) and 10(b) are respective views of another embodiment of the conventional process for manufacturing a suture needle.
Figure 10:
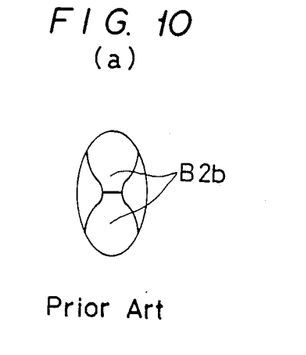

FIGS. 9(b), 9(c) and 9(d) show respective section of the suture needle body B1, in which FIG. 9(b) is an elliptical section, FIG. 9(c) is a circular section and FIG. 9 (d) is a triangular section.

As shown in FIG. 10(b), the hole means B2 comprises a hole B2a for engaging with a suture, a pair of lugs B2b and a recess B2c thereupon. The pair of lugs B2b are contacted with each other at their upper ends and formed integrally at their lower end. Such structure is suitable for inserting the suture therein.

A process for manufacturing the aforesaid conventional suture needle comprises the following steps.

(A) Step of cutting off a stainless steel wire so as to conform to the diameter and length of a desired suture needle.

(B) Step of forming one unit obtained by the above step into a elliptical section by a flattening means.

(C) Step for forming about one third (needle front part) of such a member into a triangular section, a middle portion thereof into a circular section and a rear part thereof into an elliptical section.

(D) Step of forming a hole means for inserting into, and engaging with a suture, in the rear part of such member.

(E) Step of bending the whole of such member in a semicircular form.

The aforesaid conventional technique has the following disadvantages.

(1) The suture needle obtained by the aforesaid process is a solid body and its diameter is forced to be thick to increase strength.

Such a thick needle causes a patient strong pains.

(2) When such suture needle units are produced continuously, they must be lined up correctly and then necessary mechanical processings must be provided. Accordingly, the production cost is high.

(3) If a manual operation will be adopted to avoid the inconvenience of such a line-up process, the product cost will become much higher and the quality of finished products becomes unreliable.

BRIEF SUMMARY OF THE INVENTION

It is therefore a general object of this invention to provide a suture needle having a high resilience, and its manufacturing processes enabling a continuous production.

More specifically, the present invention has the following features.

(1) A suture needle body is of a tubular construction. Namely, a hollow portion is formed in a substantially overall length of the needle body, and a suture is inserted and fixed in the hollow portion.

(2) A process for manufacturing a suture needle comprises the following steps:

(a) applying compression for a U-shaped extended metal plate to increase its resilience;

(b) forming a nearly triangular cutaway portion recessed on both walls of said U-shaped metal plate so as to produce a front part of individual needle pattern;

(c) forming a pointed end of said individual needle pattern by closing both walls of said front part;

(d) dividing a series of needle patterns combined with each other at respective pointed ends into a plurality of segmented needle bodies;

(e) grinding individual needle bodies;

(f) inserting a suture in a hollow portion of said needle body of a U-shaped section, closing said both walls of said U-shaped needle body and inserting and fixing in said hollow portion, thereby producing a suture needle;

(g) forming said suture needle in a bended form; and (h) providing said suture needle with a sterilization treatment. Other features and advantages of the invention will be apparent from the following description taken in connection with the accompanying drawings.

DETAILED DESCRIPTION OF PREFERRED EMBODIMENTS

First Embodiment:

A typical example of a suture needle according to appended claims 1 to 3 of the present invention will be described in connection with FIGS. 1 to 4.

Figures 1, 2, 3:
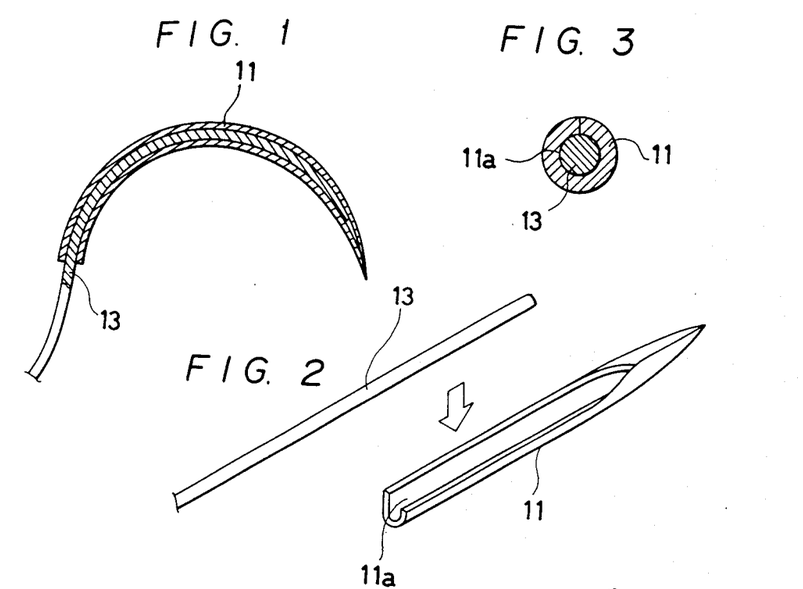
FIG. 1 is a section view of a suture needle according to this invention, in which a suture is incorporated in a groove of a needle body.
FIG. 2 is a perspective view of a condition, in which the suture is about to be inserted into the groove of the needle body in FIG. 1.
FIG. 3 is a section view of the suture needle in FIG. 1.

In FIG. 1, there is shown a needle body 11, in which a hollow portion 11a is extended through a nearly whole length of the needle body 11 and a suture 13 is inserted into the hollow portion 11a.

Figure 4:
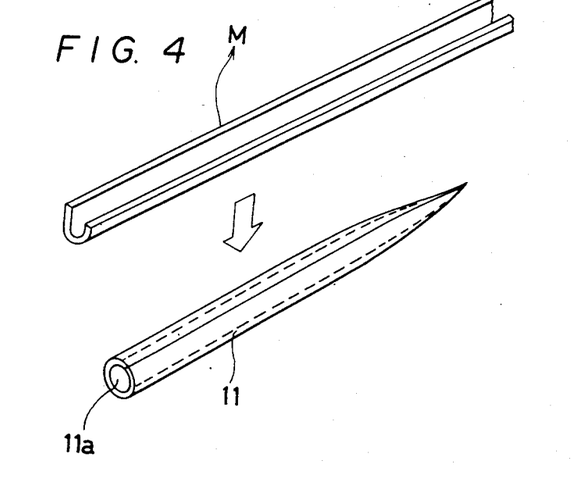
FIG. 4 is a perspective view of a condition, in which a U-shaped metal plate is transformed into a tubular needle body.

The hollow portion 11a is made of a U-shaped metal plate M as shown in FIG. 4. Thus, the hollow portion 11a is formed in a substantially overall length of the needle body 11. After the suture 13 has been inserted in the hollow portion 11a as shown in FIG. 2, both sides of the U-shaped metal plate M are caulked hermetically by a suitable press means. The section of the caulked needle body 11 is circular in this embodiment, but may be triangular or other shape.

A process for manufacturing the aforesaid suture needle will now be described in connection with FIGS. 5(a) to 7(b).

FIGS. 5(a) to 5(d) are schematic views of the process for manufacturing a large number of suture needles by press means.

Figure 6A:
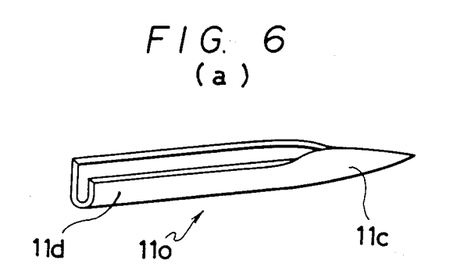
Figure 6B:
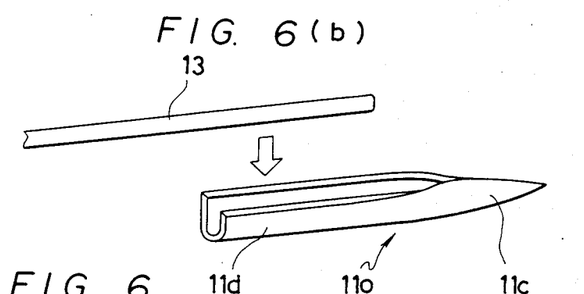
Figure 6C:
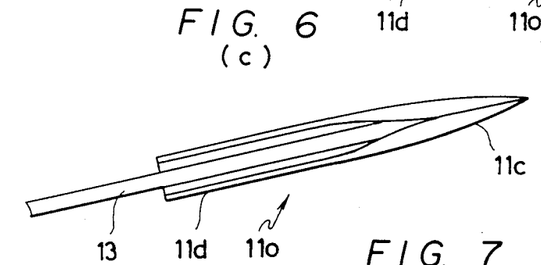

FIGS. 6(a) to 6(c) are schematic views of a segmented suture needle pattern 110, in which the suture 13 is inserted in the hollow portion.

Figure 7A:
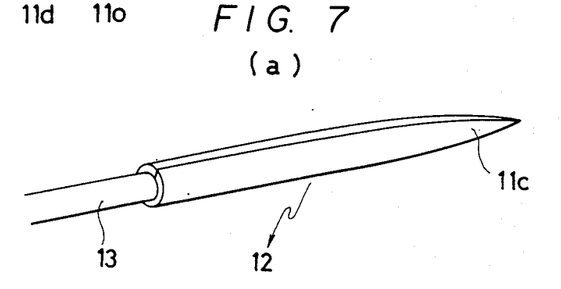
Figures 7B, 8A:
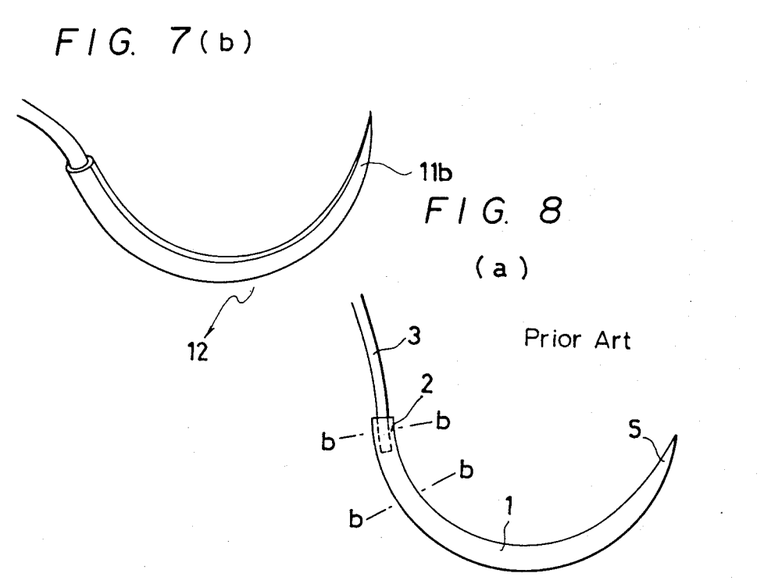
FIGS. 8(a) to 8(d) are respective views of an embodiment of a conventional process for manufacturing a suture needle.

FIGS. 7(a) and 7(b) are schematic views of a finished suture needle by the aforesaid steps.

The metal plate M made of a stainless steel (in this embodiment) may be formed from a flattened plate or may be an existing U-shaped pipe. Or, a material of the suture needle body may be made by cutting a round pipe in a semicircular section form in an axial direction.

A process for manufacturing a large number of suture needles in the case the U-shaped metal plate M is used comprises the following steps.

(A) To enhance the resilience of the metal plate M itself, it is subject to compression by a suitable press means.

Figure 5A:
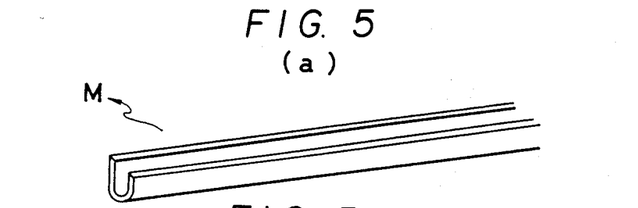
FIGS. 5(a) to 5(d), FIGS. 6(a) to 6(c) and FIGS. 7(a) and 7(b) are respective views of an embodiment of the suture needle according to the invention.
Figure 5B:
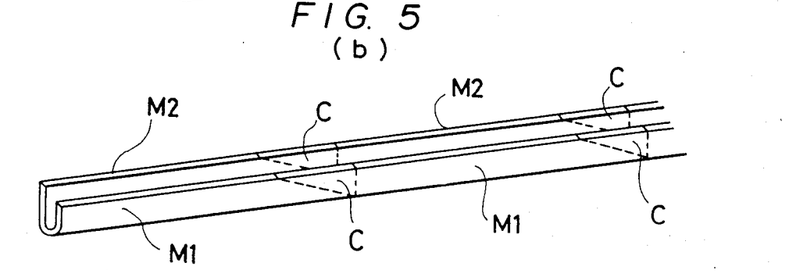
Figure 5C:
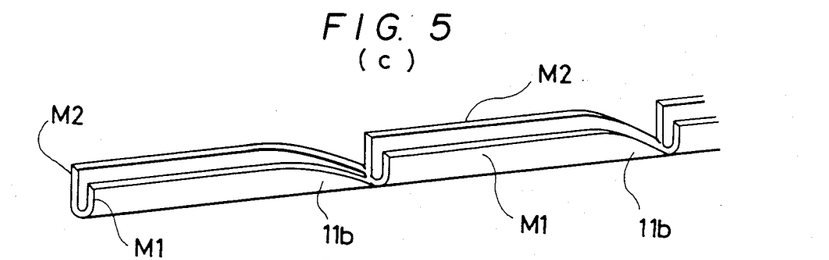

(B) Following this step, a nearly triangular cutaway portion C is formed on both walls M1 and M2 of the U-shaped metal plate M as shown in FIG. 5(b). It is formed with an equal space in a longitudinal direction of the metal plate M in order to produce a front part 11b of individual suture needle body 11.

Figure 5D:
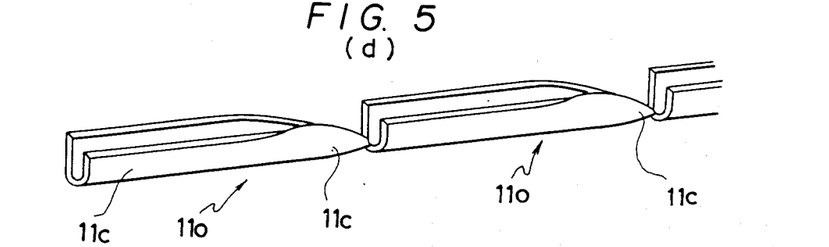

(C) Next to this step, the front part 11b is closed as shown in FIG. 5(d), thereby a pointed end 11c is formed. The section of the pointed end 11c may be circular or triangular, and the pointed end 11c is formed by press means.

(D) Next to this step, a series of the needle patterns 110 combined with each other at respective pointed ends 11c are segmented individually. A main body 11d of each needle pattern 110 excluding the pointed end 11c is of a U-shaped section as shown in Fiqs. 5(d) and 6(a) to 6(c).

(E) Each segmented needle pattern 110 as well as its pointed end 11c is ground by barrel grinding, chemical grinding or the like.

(F) Next to this step, the suture 13 having a suitable length is inserted in a U-shaped overall groove (or the main body 11d) of the needle pattern 110 as shown in FIGS. 6(b) and 6(c). The U-shaped groove is still open.

(G) Next to this step, both sides of the U-shaped needle pattern 110 are caulked hermetically by press means and the suture 13 is fixed firmly in the main body 11d, namely in the hollow portion having a circular section. Namely, the needle body is of a hollow construction extending from its pointed end to its rear end, and the suture is inserted and fixed in a substantially overall length of the needle body.

(H) Subsequently, a suture needle 12 as produced by the above steps is bent as shown in FIG. 7(b) as necessity arises.

In conclusion, the effects and aspects of a suture needle according to the first embodiment can be summarized as follows.

(1) Since a suture is inserted and fixed within a needle body throughout its substantially overall length, disengagement of the suture from the needle body is entirely prevented. Such a suture needle may be called an eyeless needle.

(2) Since the needle body is provided with a groove, it is of a tubular structure and becomes lightweight. In addition, its resilience is enhanced.

(3) Since a suture is extended through a substantially overall length of the needle body and fixed therein, even if the needle body will locally be broken within a human body, its broken part cannot be remained in it. Because the whole of the needle body is supported by the suture.

(4) Since the present invention has removed a hole structure in the prior art, cleaning and sterilization become very easy.

(5) Because of the absence of the hole structure, any cumbersome work has been removed. The products of uniform quality can be manufactured at a low cost.

Further, the effects and aspects of the process for manufacturing a suture needle according to the first embodiment can be summarized as follows.

(1) A large number of suture needles can be manufactured in a mass production system. Accordingly, productivity is very high.

(2) Since no manual operation is required in each production stage, quality of the products is constantly uniform. Thus, this invention can satisfy a demand for high reliability in medical instruments.

(3) Since a desired number of suture needles are formed from an elongaged and flattened metal plate by means of punch press, cutting, bending or the like, a desired diameter of the needle body as well as a desired sectional profile may be predetermined optionally. In addition, the production cost is inexpensive.

Second Embodiment:

A second embodiment of the invention will be described with reference to FIGS. 11 to 15(c). According to this embodiment, a large number of suture needles can be produced successively by press means.

Figure 11:
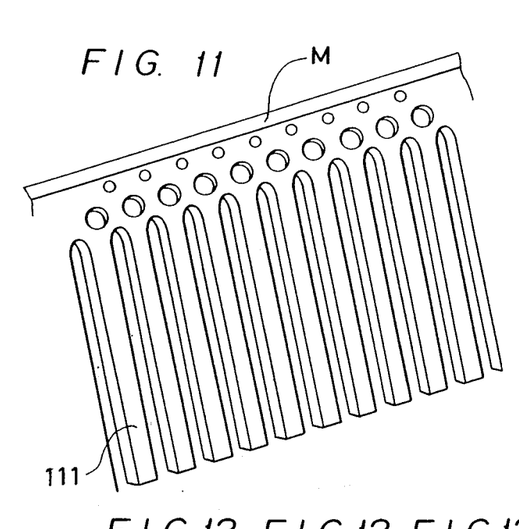
FIG. 11, FIGS. 12(a) to 12(d), FIGS. 13(a) to 13(c), FIG. 14 and FIGS. 15(a) to 15(f) are respective views of an embodiment of a process for manufaturing a suture needle according to the invention.
Figure 12:
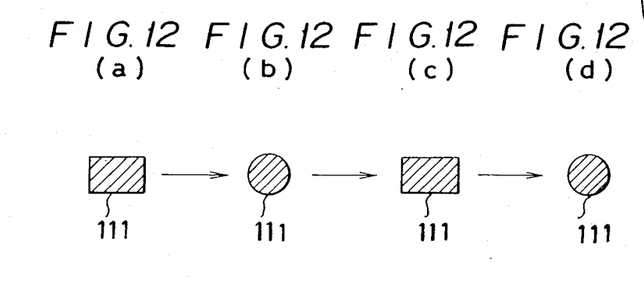

In FIG. 11 there is shown a metal plate M made of a stainless steel. The metal plate M is produced by the following steps.

(A) A large number of needle patterns 111 are formed by press and punching means as shown in FIG. 11.

Figure 13A:
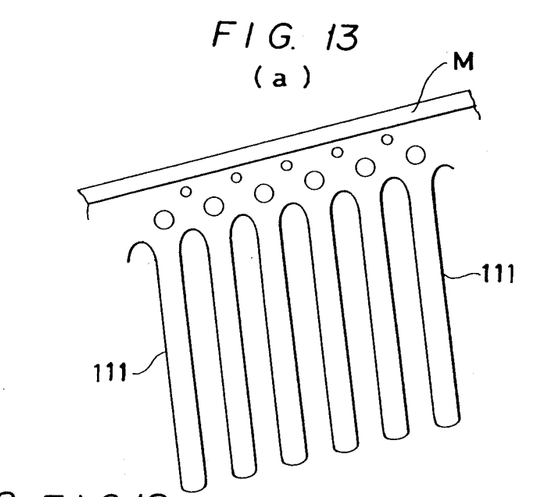

(B) Following the above step, each needle pattern 111 is compressed a few times by press means in order to increase its resilience. As shown in FIGS. 12(a) to 12(d), the section of the needle pattern 111 is transformed a few times from a rectangular shape to a round shape and from the round one to the rectangular one. Finally, the round section of it is obtained as shown in FIG. 13(a).

Figure 13B:
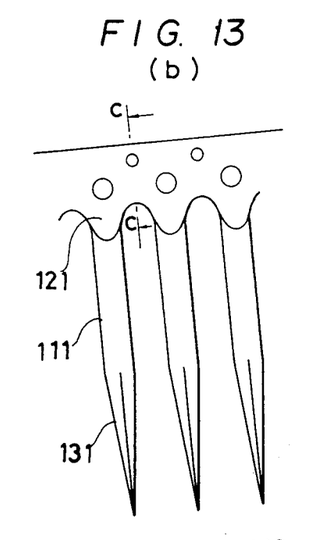
Figure 13C:
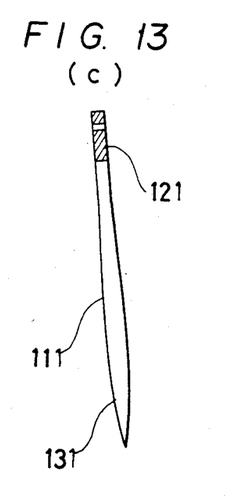
Figure 14:
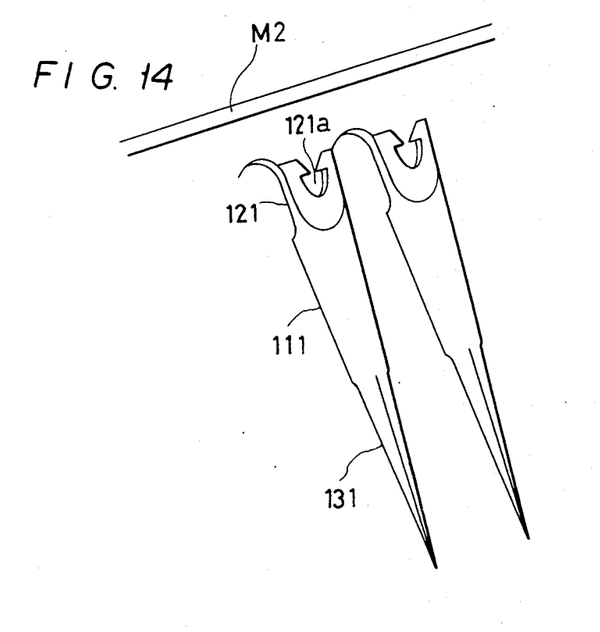

(C) Following the above step, an end of each needle pattern 111 is transformed into a pointed part 131 as shown in FIGS. 13(b) and 13(c).

(D) Following the above step, a rear part 121 of the needle pattern 111 of a round section is transformed into a flattened shape as shown in FIGS. 13(b) and 13(c).

(E) Following the above step, an opening 121a for inserting a suture is perforated on the flattened rear part 121.

Figure 15A:
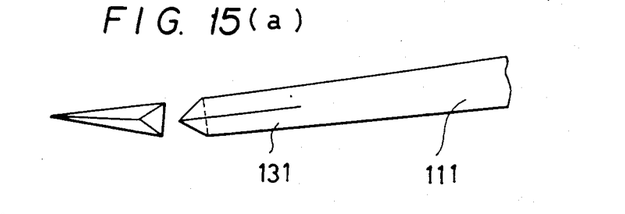
Figure 15B:
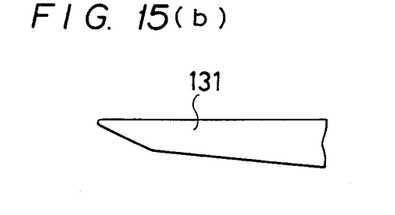
Figure 15C:
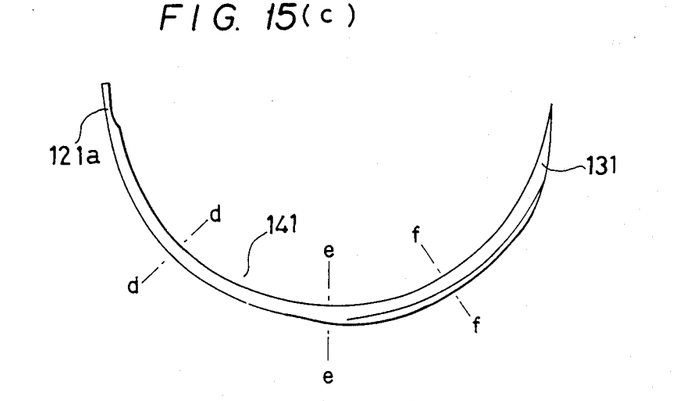
Figure 15D:
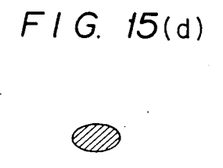
Figure 15E:
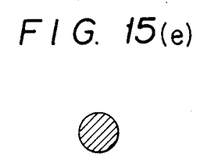
Figure 15F:
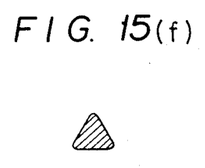

(F) After that, the pointed part 131 is ground by grinding means so as to form an edge as shown in FIGS. 15(a) and 15(c).

(G) Subsequently, the large number of needle patterns 111 jointed each other to the metal plate M are divided into individual segments. Then, each segment is bent in a suitable form, and a finished suture needle 141 is obtained. It is a solid type suture needle having an opening for inserting a suture. It is called an eye needle.

According to the second embodiment of the invention, a large number of suture needles can be produced continuously by mechanical means, so that the production cost is low and the quality of each needle unit is uniform and stable. In addition, its resilience is very strong.

What is claimed is:

1. A process for manufacturing a suture needle, comprising:
    (a) applying compression for a U-shaped extended metal plate to increase its resilience;
    (b) forming a nearly triangular cutaway portion recessed on both walls of said U-shaped metal plate so as to produce a front part of individual needle pattern;
    (c) forming a pointed end of said individual needle pattern by closing both walls of said front part;
    (d) dividing a series of needle patterns combined with each other at respective pointed ends into a plurality of segmented needle bodies;
    (e) grinding individual needle bodies;
    (f) inserting a suture in a hollow portion of said needle body of a U-shaped section, closing said both walls of said U-shaped needle body and inserting and fixing in said hollow portion, thereby producing a suture needle;
    (g) forming said suture needle in a bended form; and
    (h) providing said suture needle with a sterilization treatment.

2. A process for manufacturing a suture needle, comprising:
    (a) associating a large number of needle patterns with each other on a metal plate;
    (b) applying compression for each of said large number of needle patterns to increase its resilience by press means;
    (c) transforming a front part of each needle pattern into a triangular section shape;
    (d) transforming a rear part of each needle pattern into a flattened shape;
    (e) forming an opening for inserting a suture in the flattened rear part;
    (f) transforming said front part of said needle pattern into an edge;
    (g) dividing a series of said needle patterns combined with each other on the metal plate, into individual needle bodies to produce a needle body; and
    (h) grinding each needle body.

* * * * *